(12) United States Patent
Hunter (10) Patent No.: US 6,387,331 B1
(45) Date of Patent: May 14, 2002

(54) METHOD AND APPARATUS FOR PERFORMING MICROASSAYS

(75) Inventor: Ian W. Hunter, Lincoln, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 12 days.

(21) Appl. No.: 09/225,583

(22) Filed: Jan. 5, 1999

Related U.S. Application Data (60) Provisional application No. 60/071,179, filed on Jan. 12, 1998.

(51) Int. Cl.[7] ............................ G01N 21/03; G01N 21/01
(52) U.S. Cl. ........................ 422/102; 356/244; 356/246; 422/58; 422/82.05; 422/82.09; 422/100
(58) Field of Search .................................. 356/244, 246; 422/56, 58, 82.05, 82.09, 100, 102, 104

(56) References Cited

U.S. PATENT DOCUMENTS

| | | | | |
|---|---|---|---|---|
| 3,873,268 A | | 3/1975 | McKie, Jr. ................ 23/230 R |
| 3,894,512 A | * | 7/1975 | Ohno ........................ 118/637 |
| 4,111,754 A | | 9/1978 | Park .......................... 195/127 |
| 4,446,239 A | | 5/1984 | Tsuji et al. ................. 436/532 |
| 4,493,815 A | | 1/1985 | Fernwood et al. .......... 422/101 |
| 4,562,045 A | * | 12/1985 | Murata ...................... 422/102 |
| 4,682,890 A | * | 7/1987 | De Macario et al. ....... 356/244 |
| 4,828,386 A | | 5/1989 | Matkovich et al. ......... 356/246 |
| 4,834,946 A | | 5/1989 | Levin ......................... 422/101 |
| 5,000,921 A | | 3/1991 | Hanaway et al. ........... 422/100 |
| 5,047,215 A | | 9/1991 | Manns ....................... 422/101 |
| 5,108,704 A | | 4/1992 | Bowers et al. ................ 422/70 |
| 5,210,021 A | | 5/1993 | Goodwin, Jr. ............... 435/29 |
| 5,262,128 A | | 11/1993 | Leighton et al. ........... 422/100 |
| 5,284,753 A | | 2/1994 | Goodwin, Jr. ............... 435/30 |
| 5,290,705 A | | 3/1994 | Davis ......................... 436/164 |
| 5,453,252 A | * | 9/1995 | Truett ........................ 422/104 |
| 5,506,141 A | | 4/1996 | Weinreb et al. .......... 435/309.1 |
| 5,508,200 A | | 4/1996 | Tiffany et al. ............... 436/44 |
| 5,519,218 A | * | 5/1996 | Chang ................... 250/339.07 |
| 5,560,811 A | | 10/1996 | Briggs et al. ............... 204/451 |
| 5,770,440 A | | 6/1998 | Berndt ..................... 435/288.4 |
| 5,786,226 A | * | 7/1998 | Bocker et al. ............. 436/164 |
| 5,843,767 A | | 12/1998 | Beattie ..................... 437/287.1 |

FOREIGN PATENT DOCUMENTS

| | | |
|---|---|---|
| WO | WO 95/01559 | 7/1994 |
| WO | WO 95/11755 | 5/1995 |
| WO | WO 97/15394 | 5/1997 |

\* cited by examiner

*Primary Examiner*—Arlen Soderquist
(74) *Attorney, Agent, or Firm*—Bromberg & Sunstein LLP (57) ABSTRACT

A system and method for analyzing a plurality of liquid samples. The system has a platen having two substantially parallel planar surfaces and a plurality of through-holes dimensioned so as to maintain a liquid sample in each through-hole by means of surface tension. A source of optical radiation illuminates the through-holes, and an optical arrangement analyzes the light emanating from the through-holes. The through-holes may be individually addressable, and may have volumes less than 100 nanoliters. Samples may be drawn from a planar surface by capillary action and may be accurately dispensed, diluted and mixed in accordance with embodiments of the invention.

14 Claims, 9 Drawing Sheets

FIG. 1

FIG. 2A RECTANGULAR PACKING

FIG. 2B CLOSE PACKING

METHOD AND APPARATUS FOR PERFORMING MICROASSAYS

The present application claims priority from U.S. provisional application No. 60/071,179 filed Jan. 12, 1998, which application is herein incorporated by reference.

TECHNICAL FIELD

The present invention pertains to an apparatus and method for manipulating, transporting, and analyzing a large number of microscopic samples of a liquid or of materials including cells currently or formerly in liquid suspension.

BACKGROUND OF THE INVENTION

Chemistry on the micro-scale, involving the reaction and subsequent analysis of quantities of reagents or analytes of order microliters or smaller, is an increasingly important aspect of the development of new substances in the pharmaceutical and other industries. Such reaction and analysis may accommodate vast libraries containing as many as a million compounds to be reacted and analyzed under various conditions. Significant problems associated with current technologies as applied to chemical analysis of vast numbers (potentially on the order of hundreds of thousands or millions per day) of compounds include the problem of handling vast numbers of compounds and reactions in parallel.

Existing technology relies on 96-, 384-, or 1536-well plates containing quantities between approximately 1 microliter and 1 milliliter of liquid compound per well, and, generally, involves chemical reactions and analysis in wells disposed with single openings on flat, two-dimensional surfaces such as silicon chips. It is not practical to apply existing technology in the art to form million-well disks. There is a need, therefore, for new approaches that permit the analysis of a million samples in a laboratory format.

SUMMARY OF THE INVENTION

In accordance with one aspect of the invention, in one of its embodiments, there is provided a method for selecting samples having specified properties from a library of samples. The method has the steps of:
  a. providing a platen having two substantially parallel planar surfaces and a plurality of addressable through-holes disposed substantially perpendicularly to the planar surfaces;
  b. loading a first sample in liquid form into at least one of the through-holes;
  c. adding a second sample into the at least one of the through-holes for permitting a reaction between the first sample and the second sample; and
  d. characterizing the reaction in the through-hole in terms of the specified properties.

In accordance with alternate embodiments of the invention, each through-hole may be dimensioned so as to maintain a liquid sample therein by means of surface tension, and may have a volume less than 100 nanoliters. The plurality of addressable through-holes may have a density in excess of $10^8$ per square meter.

In accordance with further alternate embodiments of the invention, the step of loading a first sample may include drawing the sample from a planar surface by capillary action. The platen may be brought into contact with a reservoir of liquid and rotated about an axis perpendicular to the surface of the reservoir or about at least one of an axis perpendicular to the surface of the reservoir and an axis parallel to the surface of the reservoir. The method may include the further step of maintaining a humid atmosphere for preventing evaporation of the first sample or coating the liquid sample with a monolayer for preventing evaporation of the first sample.

In accordance with a further aspect of the present invention, a method is provided for preparing a plurality of combinations of members of a first set of samples in liquid form with members of a second set of samples in liquid form, the method comprising:
  a. providing a first perforated platen having through-holes and a second perforated platen having through-holes;
  b. loading a first set of samples in liquid form into the through-holes of the first perforated platen;
  c. loading a second set of samples in liquid form into the through-holes of the second perforated platen;
  d. registering the through-holes of the first perforated platen with the through-holes of the second perforated platen; and
  e. combining the first set of samples with the second set of samples.

In accordance with yet further aspects of the present invention, there are provided methods for mixing and diluting liquid samples. The methods have steps of loading one set of liquid samples into through-holes of a first platen and loading another set of liquid samples into through-holes of a second platen, and then disposing a surface of the first platen in contact with a surface of the second platen in such a way as to register at least one through-hole of the first platten with at least one of through-hole of the second platten for permitting mixing of the liquid samples of the respective sets.

In accordance with another aspect of the present invention, there is provided a system for analyzing a plurality of liquid samples. The system has a platen having two substantially parallel planar surfaces and a plurality of through-holes having apertures and walls, a source of optical radiation for illuminating at least one through-hole along an optical axis, and an optical arrangement for analyzing light emanating from the at least one through-hole.

BRIEF DESCRIPTION OF THE DRAWINGS

The foregoing features of the invention will be more readily understood by reference to the following detailed description taken with the accompanying drawings in which.

DETAILED DESCRIPTION OF PREFERRED EMBODIMENTS

Through-hole Wells

Figure 1:
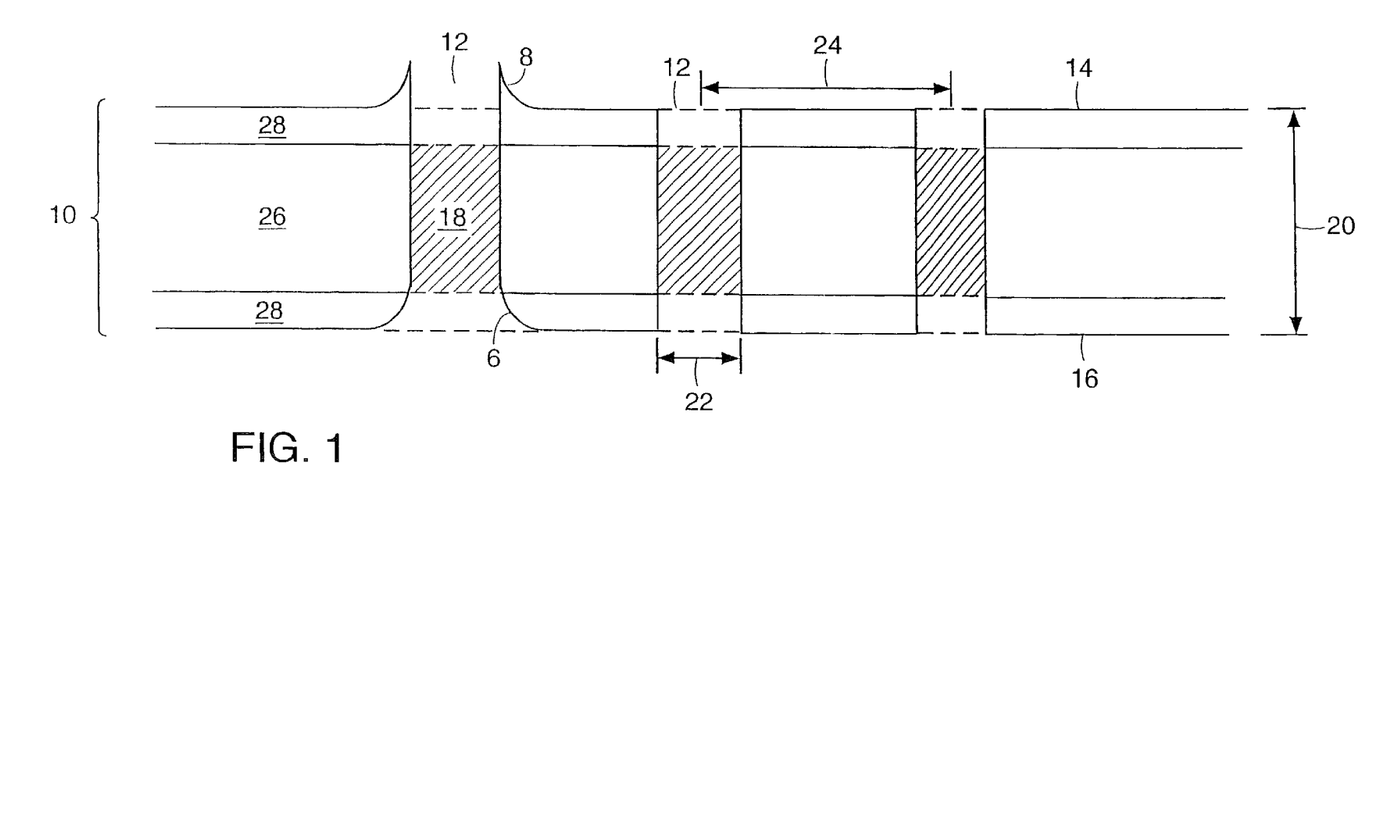
FIG. 1 is a side view in cross-section of a portion of a laminated platen containing multiple through-holes for analysis of liquid samples in accordance with a preferred embodiment of the present invention.

In accordance with a preferred embodiment of the invention, the volume of each well employed for the assay of a chemical or biochemical reaction is reduced typically to less than 100 nanoliters ($10^{-10} m^3$). The packing density of wells may thereby be increased by several orders of magnitude over prior art technology. Referring to FIG. 1, a side view is shown in cross section of a platen 10, otherwise referred to herein as a "substrate" or "sample wafer." Platen 10 is the carrier of a large number of through-holes 12 which traverse platen 10 from one surface 14 to an opposing surface 16 of the platen and constitute assay wells (or "microwells") in accordance with an embodiment of the invention. Through-holes 12 may be shaped as circular right cylinders, or, alternatively, may have rectangular cross-sections, however otherwise shaped through-holes are within the scope of the present invention. As used in the present description and in the appended claims, the term "platen" refers to a structure having substantially parallel plane surfaces and transverse dimensions substantially exceeding the thickness of the structure between the substantially parallel plane surfaces.

The apertures of through-holes 12 need not be square, and, in accordance with an alternate embodiment of the present invention, flanges 8 may extend above planar surface 14 surrounding some or all of through-holes 12 while indentations 6 may be fabricated rounding the edges of through-holes 12 at opposing surface 16. Flanges 8 and indentations 6 may advantageously provide for registration of successive platens 10, in the case where platens are stacked, and in processes of mixing or dilution, as discussed in detail below in reference to FIGS. 9–10.

In accordance with an embodiment of the invention, through-holes 12 are loaded with a first sample 18 in liquid form. Sample 18 is allowed to react with a second sample where the second sample may include a variety of test samples and by subsequent or concurrent analysis of the reaction products, using, for example, optical markers, a large number of reactions may be processed and analyzed in parallel.

As applied to biological assays, by way of example, first sample 18 may be a reagent, including, for example, cells in aqueous suspension, eukaryotic (animal, yeast) or prokaryotic (bacteria) cells, hybrid cells, and biological molecules including, for example, antibodies and enzymes, although application to other biological or non-biological assays is within the scope of the invention as claimed herein. All such reagents may also be referred to herein and in the appended claims as "targets." Typical yeast cell concentrations of $10^7$ cells per milliliter of solution yield on the order of 1000 cells per 100 nanoliter well. Typically, an entire chip or the subset of through-hole wells constituting a contiguous region of platen 10 may be populated with a single strain of cells.

A typical procedure assay procedure, such as may be employed in pharmaceutical research, entails the subsequent addressed introduction of a test sample including one or more analytes into the through-hole wells, with selected materials introduced into subsets of through-holes that may include one or more through-holes. The test sample addressably introduced into the subsets of through-holes may contain drug candidates or known drugs. The test sample may be comprised of multiple components, introduced at the same time or sequentially. Components of the test sample may include analytes, antagonists, reagents, solvents, or any other materials and may be introduced in liquid form or otherwise. In accordance with a preferred embodiment of the invention, test samples are introduced into the through-hole wells in liquid form in order to facilitate rapid reaction via diffusion with first sample 18 already resident in liquid form in the through-holes.

The set of substances from which the second sample addressed to a particular through-hole site is drawn is referred to in this description and in the appended claims as a "library" of substances. In typical applications, the library is of a substantial size and thus advantageously utilizes the capability of the present invention to facilitate parallel reaction and analysis of large numbers of substances. In pharmaceutical applications in particular, libraries may be composed of between $10^3$ and $10^9$ substances and combinations of substances.

Figure 2A:
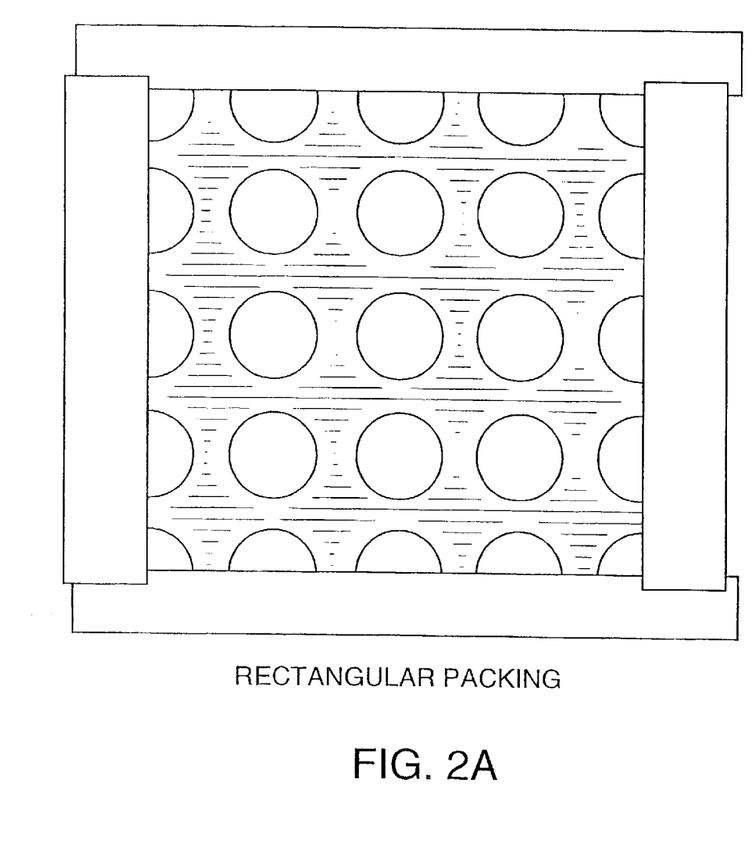
FIG. 2A is top view of a portion of the platen of FIG. 1 in which the through-holes are configured on rectangular centers.
Figure 2B:
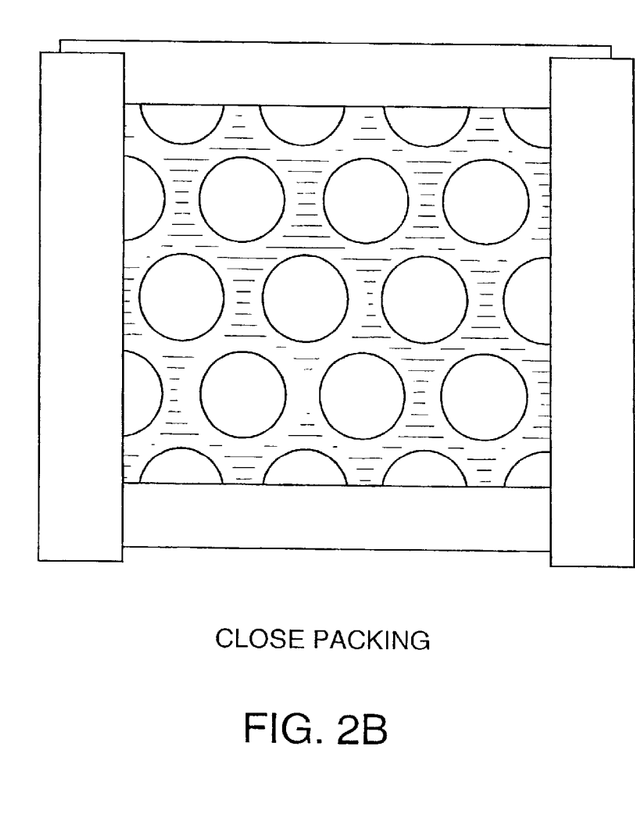
FIG. 2B is top view of a portion of the platen of FIG. 1 in which the through-holes are configured in a hexagonal close-packed array.

A typical thickness 20 of platen 10 is on the order of 1–2 mm, while through-holes 12 have typical characteristic dimensions (such as diameters) 22 of on the order of 100–400 $\mu$m. Thus the volume of each through-hole 12 between surface 14 and surface 16 is on the order of ~$10^{-7}$ $cm^3$ or greater. Through-holes 12 are spaced on centers typically on the order of twice the diameter of the holes, although all spacing configurations are within the scope of the invention and of the appended claims. In particular, through-holes 12 may be centered on a rectangular grid, as shown in FIG. 2A, or in a close-packed hexagonal lattice, as shown in FIG. 2B.

Figure 3:
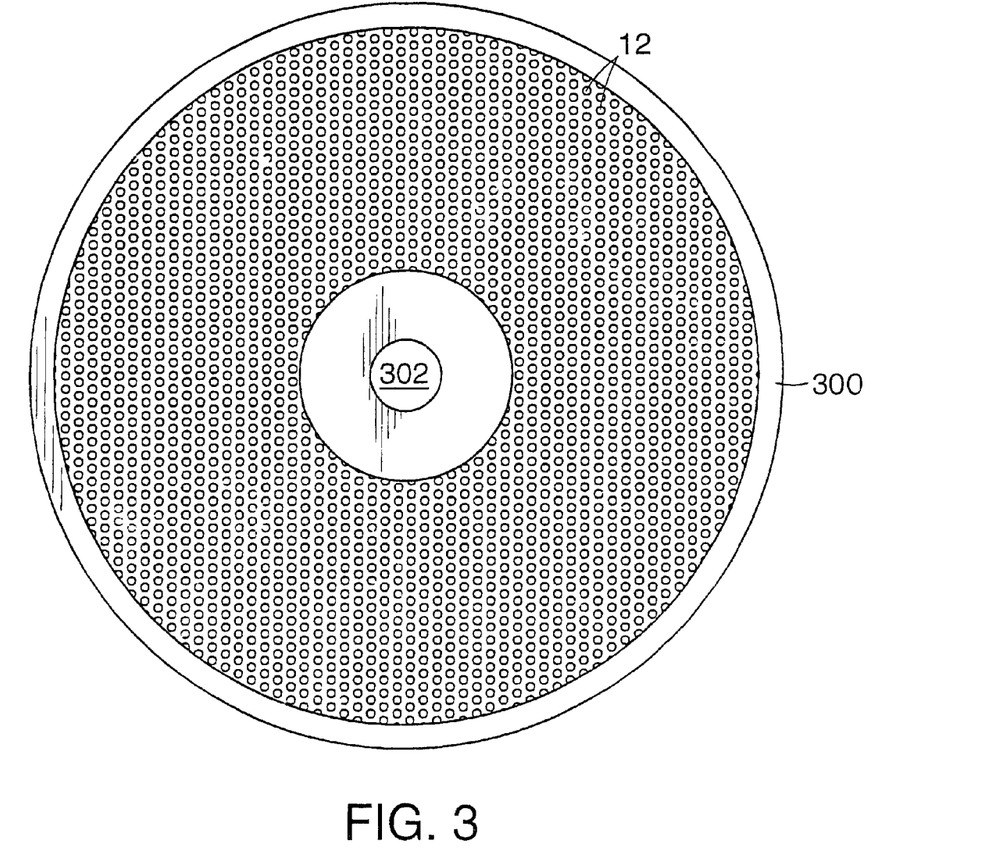
FIG. 3 is a top view of round sample wafer populated with through-holes in accordance with an embodiment of the present invention.

In accordance with an alternate embodiment of the present invention described with reference to FIG. 3, through-holes 12 may be disposed in an array within a circular sample wafer 300 having a central hole 302 for purposes of centering with respect to handling equipment.

Referring again to FIG. 1, platen 10 may be any solid or quasi-solid material into which through-holes 12 may be formed. In particular, in accordance with various embodiments of the invention, platen 10 may be formed from metal, semiconductor, glass, quartz, ceramic or polymer materials, all given without limitation by way of example. In accordance with a preferred embodiment of the invention, platen 10 is formed in a format associated with a compact disk read-only-memory (CD-ROM)—namely that of a polymer disk, approximately 1.2 mm in thickness, and approximately 100 mm in diameter.

Platen 10 may also advantageously be formed of a laminate of materials, with a central layer 26 and outer "sandwiching" layers 28. Advantages of this construction for containment of sample 18 will be discussed further below.

Through-holes 12 may be formed in platen 10 by means appropriate to the material of platen 10. Through-hole forming methods include, by way of example, laser ablation by means of an ultraviolet (UV) excimer laser which may form 100 μm through-holes in glasses and polymers. Additional through-hole forming techniques include mechanical drilling, electrochemical methods, or selective chemical or charged-particle etching techniques. Additionally, microcapillary bundles of glass fibers of varying compositions may be drawn from preform and sliced to form platens, and then selectively etched to form through-holes.

Loading the Through-hole Microwells

Figure 4:
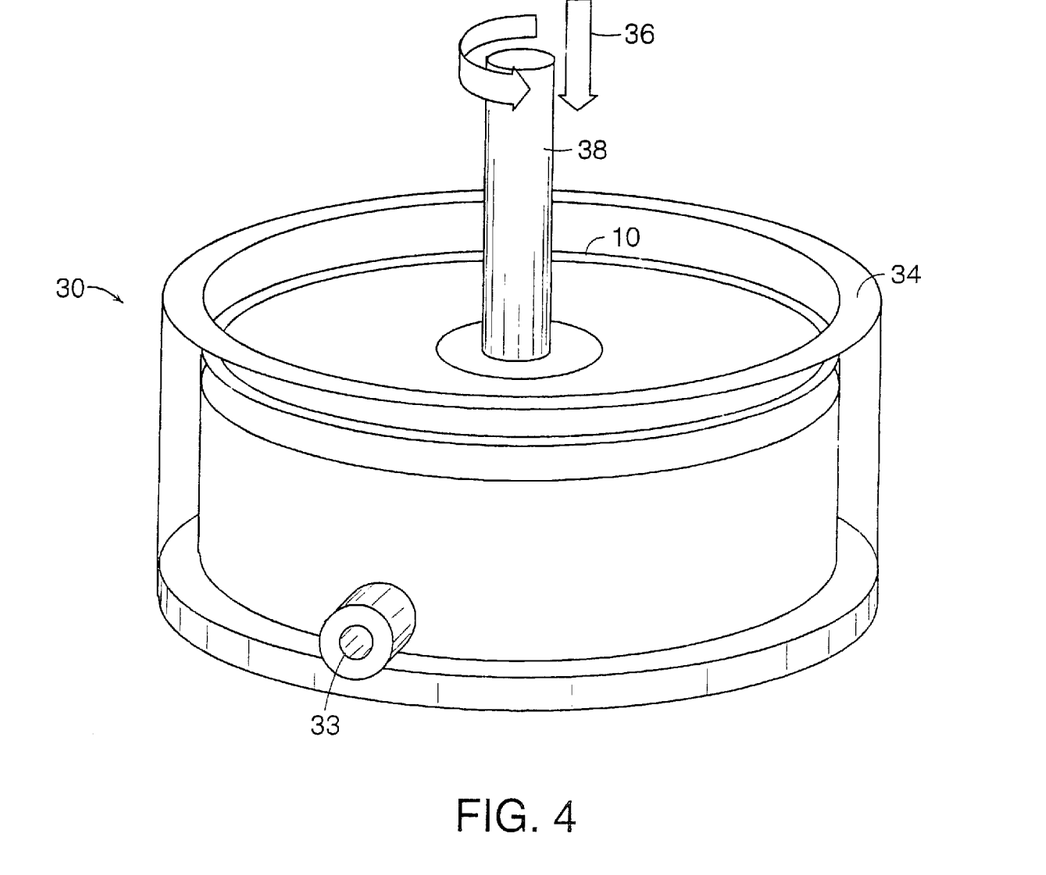
FIG. 4 is a side perspective view of an arrangement for loading a liquid sample into the platen of FIG. 1 by employing capillary and inertial insertion forces.

On the size scale employed in accordance with embodiments of the invention, where through-holes 12 have aspect ratios of axial length to diameter greater than unity, viscous forces may dominate inertial forces in governing the fluid kinetics of material in the through-hole wells. Consequently, capillary action may be employed to populate through-holes 12 with sample fluid 18. Referring to FIG. 4, two aspects of loading the through-hole wells are described with reference to a sample insertion apparatus 30. Since through-hole microwells 12 are open at both sides, insertion of liquid into the wells does not require that the air displaced by the liquid on insertion flow through the entering fluid, as occurs in the prior art well structure having only a single aperture for influx of liquid and efflux of displaced air. Liquid 32, loaded into reservoir 34 via port 33, may, as discussed above, contain cells or other particles in suspension. Liquid 32 may be forced into through-hole microwells 12 (shown in FIG. 1) by in-line impulsion as by driving platen 10 into liquid 32 by force applied along direction 36 transverse to the plane of platen 10. The transverse piston force may be applied via shaft 38 or in any other manner known in the mechanical arts.

In accordance with another embodiment of the invention, liquid may also be loaded through capillary action of liquid 32 along the walls of the through-holes. To provide for wetting of the lower surface of platen 10, the platen is lowered into reservoir 34 and rotated, by torque applied through shaft 38, or otherwise, through an angle typically on the order of a quarter evolution. Alternatively, platen 10 may be wetted and liquid 32 drawn into the microwells by immersing platen 10 into liquid 32 and tilting the platen about an axis in the plane of the platen.

Stabilization with Respect to Capillary and Evaporative Liquid Loss

In order to maintain the sample in liquid form in the respective microwells, evaporation of the liquid must be avoided. One method of avoiding evaporation is to provide an ambient atmospheric environment of 100% humidity. Among other methods that may be practiced to suppress evaporation, in accordance with an embodiment of the invention, a high molecular-weight fluid, such as various alcohols, for example, may be introduced on each end of the microwells thereby forming molecular monolayers or other thin layers to prevent evaporation of the liquid sample.

Figure 5:
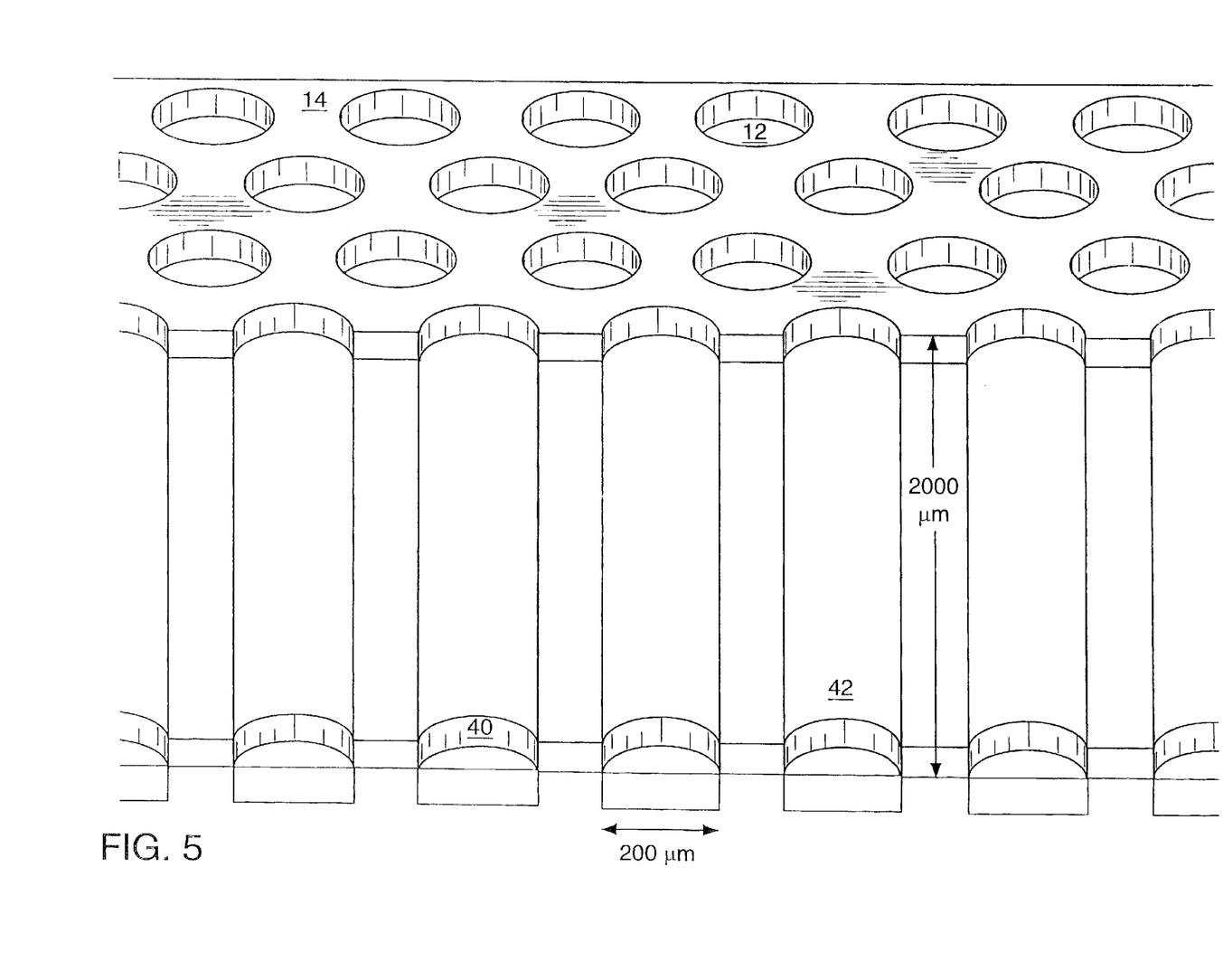
FIG. 5 is a cut-away view of a single through-hole in the platen of FIG. 1, showing the use of hydrophobic and hydrophilic layers for containment of an aqueous sample.

Referring to FIG. 5, a cross-section of a portion of platen 10 is shown to include through-hole microwell 12. In order to enhance capillary loading of the microwell and to prevent capillary outmigration of the sample liquid, exterior sections 40 of the microwell, adjacent to surfaces 14 and 16 of platen 10, has a hydrophobic wall surface in accordance with a preferred embodiment of the invention, while the interior section 42 of the through-hole wall has a hydrophilic surface thereby preferentially attracting an aqueous liquid sample. Typically, the interior ~160 μm segment of the microwell may have a hydrophilic wall surface, while the hydrophobic layers on either end of the well are on the order of 20 μm in length. On loading the sample liquid into the microwells, typically 10% of the well, on either end, is left unfilled, and subsequent test samples in liquid form will rapidly diffuse to hydrophilic center of microwell thereby mixing with the liquid already present.

Optical Interrogation

Depending upon the application to which the present invention is applied, the result of the reaction of the first sample in liquid form with subsequently added analytes may be read out in a wide variety of manners known to persons skilled in the biological or biochemical arts. Readout systems may employ taggants of various sorts allowing interrogation of the sample within the addressable microwell to determine whether a specified reaction has occurred. Some reactions may be interrogated optically, to include, without limitation, such optical methods as colorimetric or fluorometric methods, or resonant or non-resonant scattering methods, including Raman spectroscopic methods.

Figure 6:
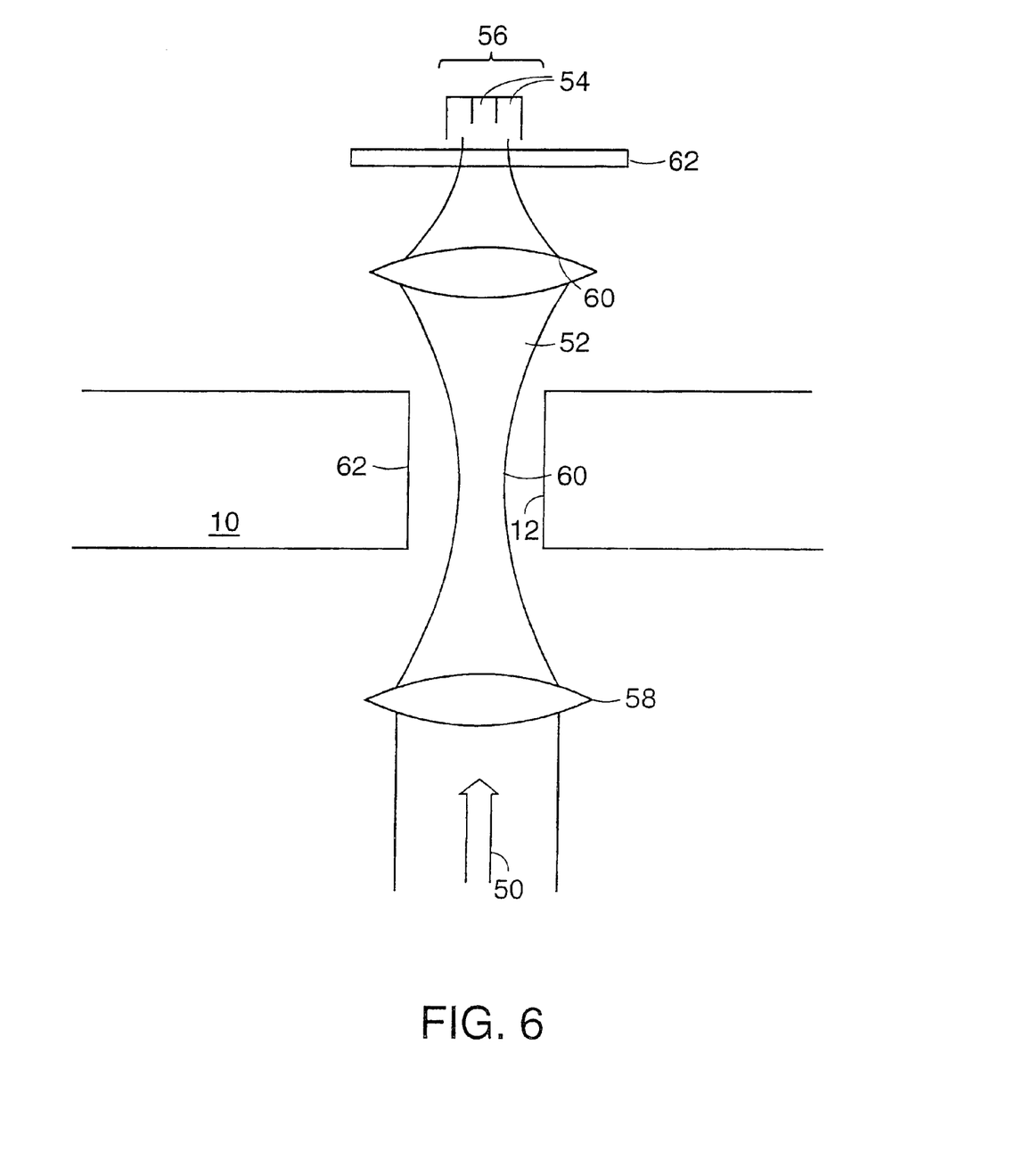
FIG. 6 is schematic diagram of a confocal optical arrangement for interrogation of a liquid sample in a through-hole in accordance with an embodiment of the present invention.

Referring now to FIG. 6, optical interrogation methods, of which the foregoing are but examples, may be implemented, in accordance with an embodiment of the invention by coupling a light beam 50 into through-hole 12 of platen 10 and detecting light 52 emergent from the opposite aperture of through-hole 12 by detectors 54 constituting detector array 56. Alternatively, light returned by scattering in the original direction can be collected and analyzed using standard optical techniques. In order to optimize the signal-to-noise of the optical signal, the beam shape and through-hole volume are preferably matched. In accordance with a preferred embodiment of the invention, optical matching to a through-hole of cylindrical cross-section and of aspect ratio greater than one is achieved through a confocal optical geometry in which an initially collimated beam 50 is transformed by optical element 58 into a beam having a diffraction limited focus at the center 60 of through-hole 12. The emergent optical beam 52 is collected and focussed onto detector array 56 by optical element 60. Superior optical sampling of the volume of the through-hole may be obtained if the through-hole has a rectangular cross-section, and if the optical radiation is guided by the walls of the through-hole in the manner of a waveguide. Optical element 58 and 60 may be lenses or mirrors or combinations thereof as well known to persons skilled in the optical arts. Detector array 56 may be a charge-coupled device (CCD) array, for example, and, in one embodiment of the invention, a 1000× 1000 element format is employed, with each through-hole imaged onto three elements 54 of the detector array. A window 62 may be disposed between platen 10 and detector array 56 and may be dried using standard techniques if the assay is conducted in a humid ambient environment as discussed above. Alternatively, beam 50, coupled into through-hole 12 by coupling element 58 may be guided, in the manner of a guided wave through a waveguide, by the walls 62 of through-hole 12 in order to provide efficient interrogation of the sampled volume within the through-hole.

In some cases, where the material of platen 10 is not entirely opaque at the wavelengths of interrogating optical beam 50, wall 62 of through-hole 12 may be coated to prevent light leakage and cross-talk among the addressable sample volumes.

Figure 7:
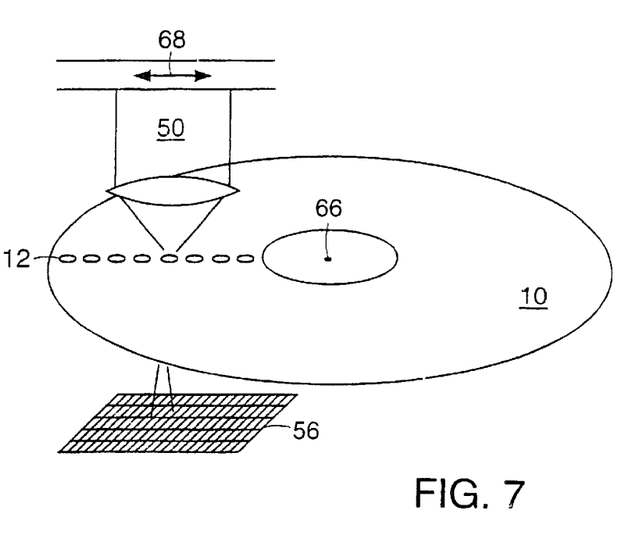
FIG. 7 is perspective view of a scanning arrangement for serially interrogating liquid samples retained in through-holes of a disk-type platen in accordance with an embodiment of the present invention.

FIG. 7 shows a preferred embodiment of the present invention in which platen 10 is configured in the CD-ROM format described above, with interrogating optical source 50 capable of travel in radial direction 68 while platen 10 rotates about center 66. Optical detector array 56 may translate in conjunction with source 50, in accordance with an embodiment of the invention.

Continuous Process Analysis

Figure 8:
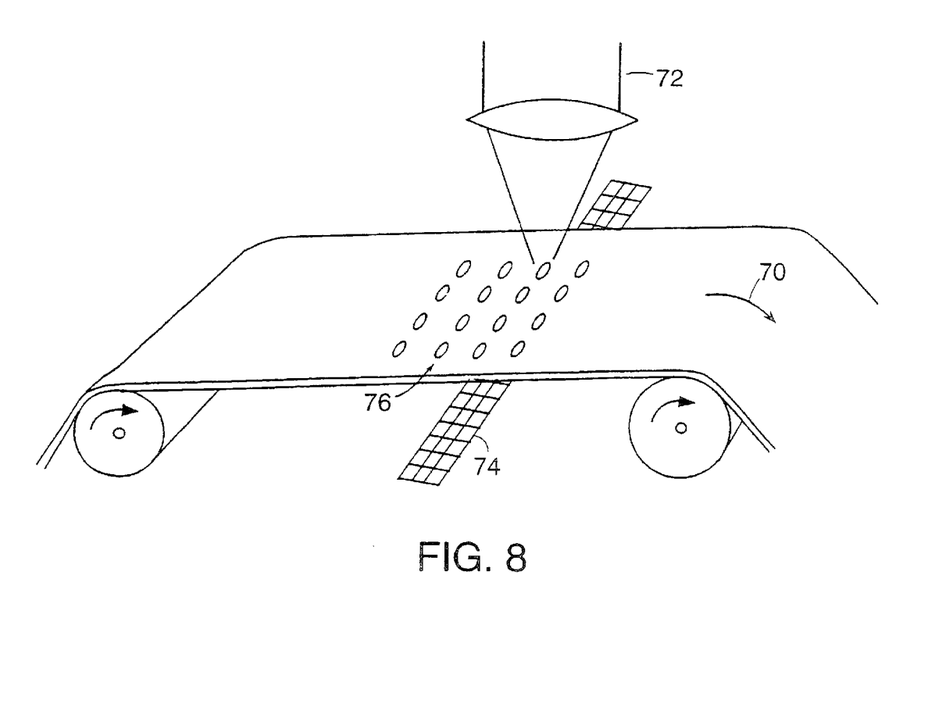
FIG. 8 is schematic representation of a scanning arrangement for serially interrogating liquid samples retained in a continuous-process film-type platen, in accordance with an alternate embodiment of the present invention.

Referring to FIG. 8, in accordance with an advantageous embodiment of the present invention, platen 10, which may be a flexible polymeric substance, for example, is conveyed in a direction 70 past an optical interrogation system comprising an optical source 72 and a detector array 74. Samples in liquid form may be loaded into through-holes 12 and advanced at a rate governed by the relevant reaction times so that a row 76 is interrogated optically at the period during which a specified indication is expected.

Mixing and Dilution

Figure 9:
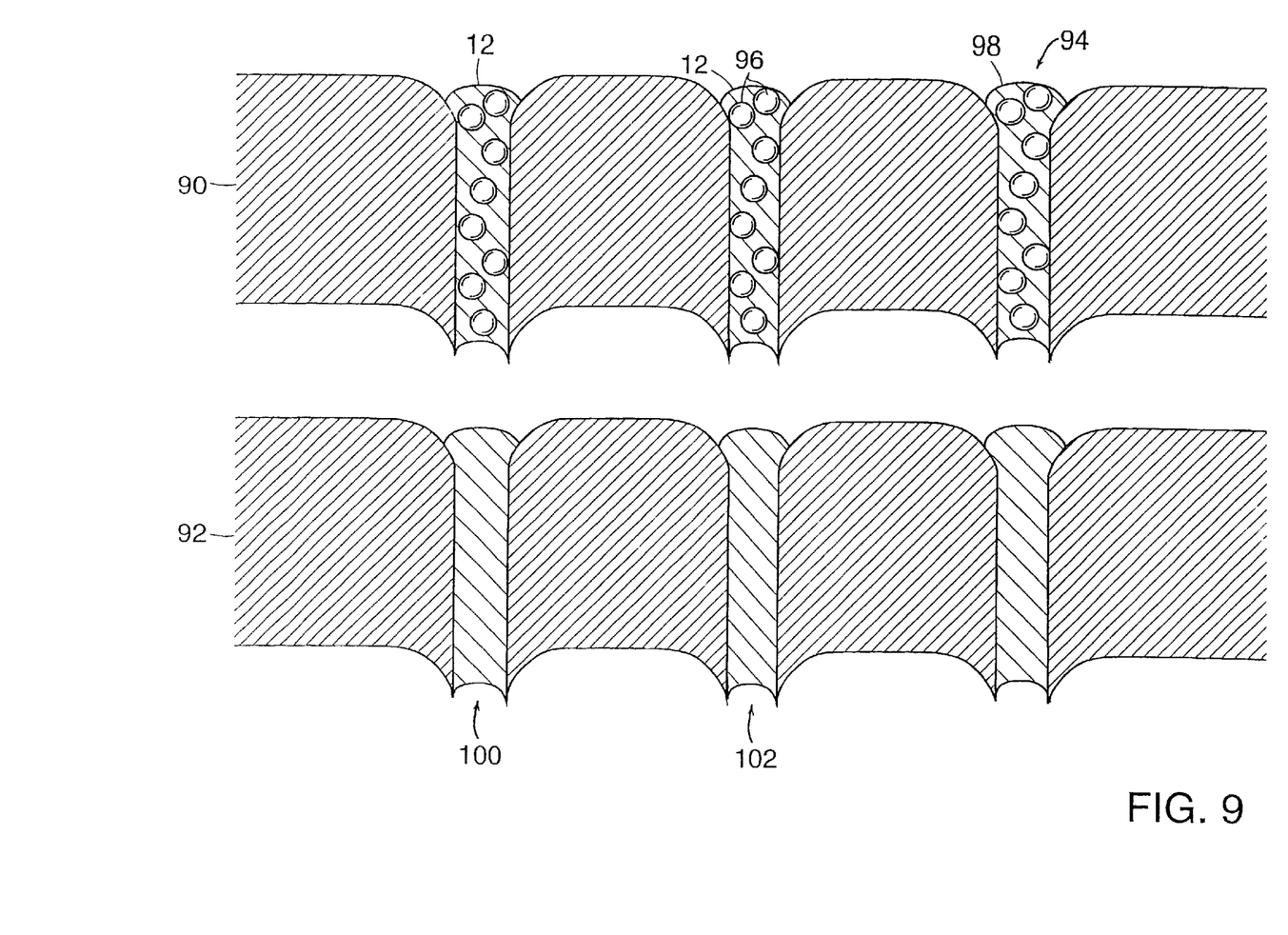
FIG. 9 is a cross-sectional view of portions of two platens brought into proximity with through-hole registration in anticipation of mixing or dilution in accordance with embodiments of the present invention.

Referring now to FIG. 9, a cross-sectional view is shown of portions of a first platen 90 and a second platen 92 brought into proximity with each other in anticipation of processes performed in accordance with embodiments of the present invention for preparing, mixing, or diluting liquid samples. Through-holes 12 of platen 90 are shown as having been loaded with liquid samples 94 which may be identical across some specified subset of through-holes 12, or may be identical for the entire platen. Liquid sample 94, as shown schematically, may include cells or other targets 96 in solution within a solvent 98.

Through-holes 12 of second platen 92 is shown as having been loaded with liquid samples 100 and 102 shown comprising one or more solvents or other agents. In particular, platen 92 may have been populated with a library of distinct compounds, each of which is to be exposed to target 96 of platen 90.

Figure 10:
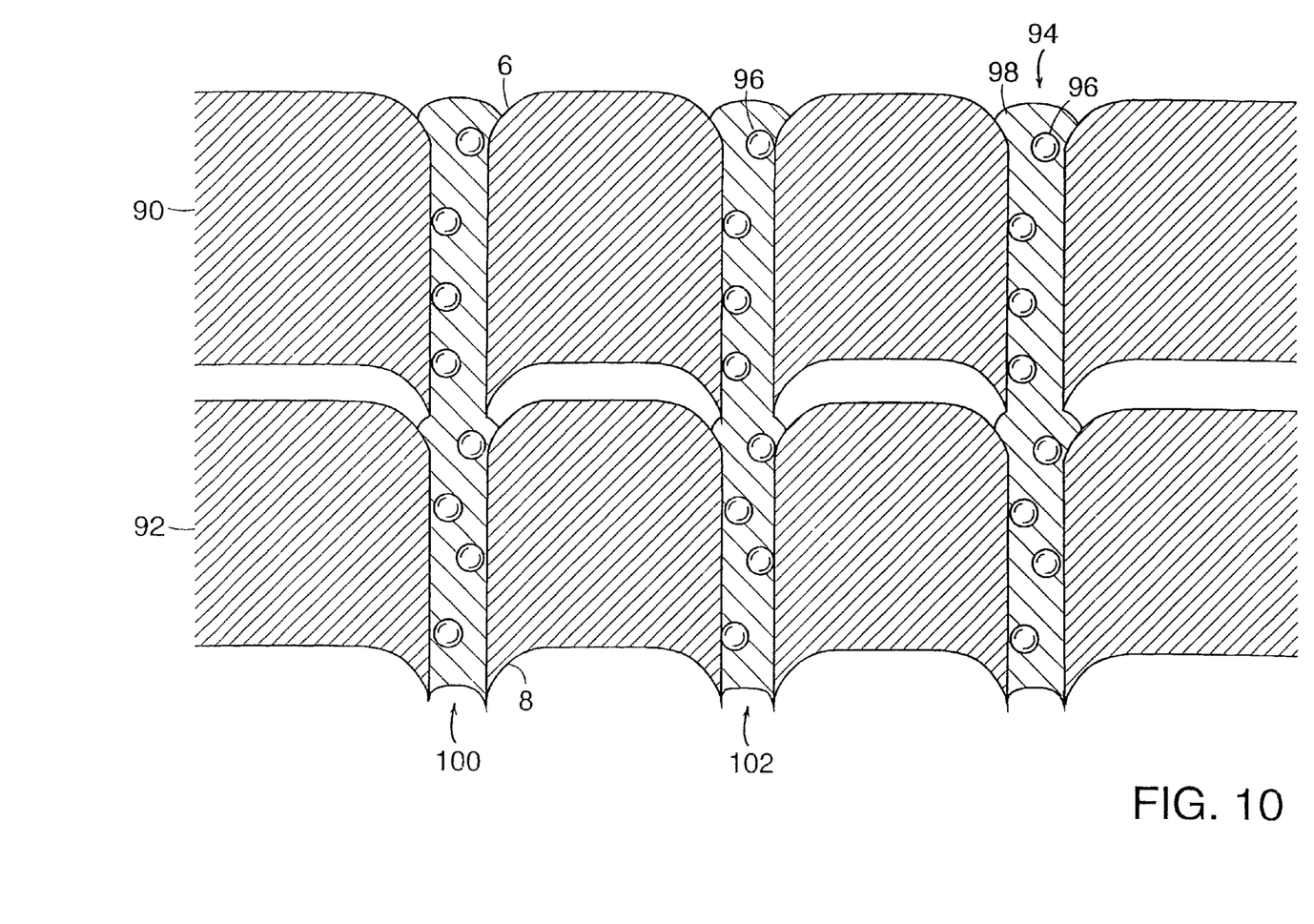
FIG. 10 is a cross-sectional view of the portions of two platens of FIG. 9 after the two platens have been brought into contact to facilitate mixing or dilution.

FIG. 10 shows platens 90 and 92 of FIG. 9 having been brought into contact with one another, in such a manner as to allow through-holes of the respective platens to register on a one-to-one basis. The mating of protrusions 8 with indentations 6 of respective platens facilitates the registration of through-holes, and provides for the mixing of the liquid sample contents of the respective through-holes. Thus, as shown, half of targets 96 from samples 94 of first platen 90 have migrated to the solvent of samples 100 and 102. Mixing or dilution may be facilitated in this manner, either through ordinary statistical diffusion, or by any method employed to facilitate mixing. Mixing may be enhanced, for example, by the creation of thermal eddy currents and turbulence induced by laser irradiation. Mixing rates have been found to be enhanced in this way by more than an order of magnitude. Any other mixing techniques, including acoustic perturbation or stirring of the samples with micropipettes, for example, are within the scope of the present invention as described herein and as claimed in any appended claims.

The number of platens 90 and 92 that may be stacked, in accordance with the present invention, is not limited to two, as shown in FIGS. 9 and 10 by way of example only. Thus, the concentration of targets 96 in solvent 98 may be diluted to a specified degree by stacking a corresponding number of platens with registered through-holes and allowing migration of targets 96 throughout the liquid contained within the corresponding sample volumes of the stack.

Transportation of Biological Samples

The perforated platen described herein in accordance an embodiment of the present invention may be employed, for example, for shipping samples of a uniform strain of cells to laboratories. In this application, the cells or other biological sample may be introduced into the through-hole wells of the invention in aqueous or other liquid suspension. The liquid carrier is then evaporated, allowing the cells or other biological samples to form a coating, in the form of a chimney, of the walls of the plurality of through-hole wells. The samples may then subsequently be resuspended by wetting and further analytes may be introduced.

The described embodiments of the invention arc intended to be merely exemplary and numerous variations and modifications will be apparent to those skilled in the art. All such variations and modifications are intended to be within the scope of the present invention as defined in the appended claims.

I claim:

1. A perforated platen having substantially parallel planar surfaces for manipulating distinct liquid samples, each sample having a volume less than 1 microliter, the platen comprising:
   a. an inner layer of hydrophilic material;
   b. two outer layers of hydrophobic material coupled to opposite sides of the inner layer in such a manner as to isolate the distinct liquid samples from each other; and
   c. a two-dimensional array of through-holes for retaining the distinct liquid samples, the through-holes each having a characteristic cross-sectional dimension of between 100 and 400 micrometers, the through-holes spaced on a two-dimensional grid with a center-to-center spacing between nearest neighbors of twice the characteristic cross-sectional dimension or less, each through-hole traversing the inner layer and the two outer layers in a direction substantially perpendicular to the planar surfaces of the platen,
wherein the platen has a substantially circular shape and includes a central aperture.

2. A system for analyzing a plurality of distinct liquid samples, the system comprising:
   a. a platen having two substantially parallel planar surfaces and a two-dimensional array of through-holes, the platen having apertures and walls for retaining the distinct liquid samples in such a manner that the distinct liquid samples may not intermix, the through-holes each having a characteristic cross-sectional dimension of between 100 and 400 micrometers;
   b. a source of optical radiation for illuminating a plurality of through-holes of the two-dimensional array; and
   c. an optical arrangement including a detector array for separately analyzing light emanating from each of the plurality of illuminated through-holes.

3. A system according to claim 2, wherein the apertures of the plurality of through-holes are disposed on centers of a hexagonally close-packed lattice on the surface of the platen.

4. A system according to claim 2, wherein the apertures of the plurality of through-holes are disposed on centers of a rectangular lattice on the surface of the platen.

5. A system according to claim 2, wherein the through-holes have an aspect ratio of axial to transverse dimension of greater than 1.5.

6. A system according to claim 2, wherein the volume enclosed by the wall of each through-hole and the planes of the planar surfaces of the platen is less than 100 nanoliters.

7. A system according to claim 2, wherein the wall of each through-hole is in part hydrophilic and in part hydrophobic.

8. A system according to claim 2, wherein the wall of each through-hole comprises:
   a. a central hydrophilic segment; and
   b. two hydrophobic segments such that one hydrophobic segment extends from the central hydrophilic segment to each planar surface of the platen.

9. A system according to claim 2, wherein the platen is a laminate having a central hydrophilic layer and two outer hydrophobic layers disposed on opposite sides of the central hydrophilic layer.

10. A system according to claim 2, wherein the platen is a metal.

11. A system according to claim 2, wherein the platen is a material selected from the group consisting of amorphous materials, ceramic, glass, quartz, and glassy carbon.

12. A system according to claim 2, wherein the platen is a polymeric material.

13. A system according to claim 2, wherein the walls of the plurality of through-holes are coated for allowing emission of light from the through-holes only at the planar surfaces of the platen.

14. A system according to claim 2, further including an advancement mechanism for translating the platen in a direction perpendicular to the optical axis.

* * * * *